United States Patent
Needham et al.

(10) Patent No.: US 8,740,077 B2
(45) Date of Patent: *Jun. 3, 2014

(54) MEDICATION RECORDING DEVICE

(71) Applicant: Intel-GE Care Innovations LLC, Roseville, CA (US)

(72) Inventors: Bradford H. Needham, North Plains, OR (US); Kevin Rhodes, Beaverton, OR (US)

(73) Assignee: Intel-GE Care Innovations LLC, Roseville, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/902,452

(22) Filed: May 24, 2013

(65) Prior Publication Data
US 2013/0261408 A1 Oct. 3, 2013

Related U.S. Application Data

(63) Continuation of application No. 11/941,959, filed on Nov. 18, 2007, now Pat. No. 8,448,846.

(51) Int. Cl.
*G06K 7/10* (2006.01)
*G06K 7/14* (2006.01)

(52) U.S. Cl.
USPC . 235/454; 235/375; 235/462.41; 235/462.45; 235/472.01

(58) Field of Classification Search
USPC .......... 235/375, 454, 462.01, 462.24, 462.41, 235/462.45, 462.14; 705/2, 3
See application file for complete search history.

(56) References Cited

U.S. PATENT DOCUMENTS

| | | | |
|---|---|---|---|
| 5,408,443 A | 4/1995 | Weinberger | |
| 5,752,235 A | 5/1998 | Kehr | |
| 5,845,264 A * | 12/1998 | Nellhaus | 705/28 |
| 7,806,852 B1 * | 10/2010 | Jurson | 604/65 |
| 2002/0026330 A1 | 2/2002 | Klein | |
| 2004/0052418 A1 * | 3/2004 | DeLean | 382/209 |
| 2004/0172283 A1 * | 9/2004 | Vanderveen et al. | 705/2 |
| 2006/0088196 A1 * | 4/2006 | Popovich et al. | 382/128 |
| 2006/0169773 A1 | 8/2006 | Lyons et al. | |
| 2007/0294105 A1 * | 12/2007 | Pierce | 705/2 |
| 2008/0000979 A1 * | 1/2008 | Poisner | 235/462.01 |
| 2008/0004904 A1 * | 1/2008 | Tran | 705/2 |
| 2008/0177568 A1 | 7/2008 | Kotidis | |
| 2009/0048871 A1 | 2/2009 | Skomra | |
| 2011/0021983 A1 * | 1/2011 | Jurson | 604/93.01 |
| 2012/0287255 A1 * | 11/2012 | Ignatovich et al. | 348/78 |

OTHER PUBLICATIONS

Lundell, Jay, "Why Elders Forget to Take Their Meds: A Probe Study to Inform a Smart Reminding System", Smart Homes and Beyond, IOS Press, 2006, (2006), pp. 98-105.
Labhard, Michael E., "intelligent Medtracker", U.S. Appl. No. 11/771,339, filed Jun. 29, 2007.
Kimel, Janna C. et al., "Mobile Medication", U.S. Appl. No. 11/644,016, filed Dec. 22, 2006.
Dishongh, Terrance J., "Contextual Medication Prompting Pillbox", U.S. Appl. No. 11/644,017, filed Dec. 22, 2006.
Poisner, David I., "Method for Identifying Pills via an Optical Device", U.S. Appl. No. 11/477,676, filed Jun. 30, 2006.

* cited by examiner

*Primary Examiner* — Tuyen K Vo
(74) *Attorney, Agent, or Firm* — Pillsbury Winthrop Shaw Pittman LLP

(57) ABSTRACT

A device and method for recording medication to be introduced into a body.

26 Claims, 2 Drawing Sheets

MEDICATION RECORDING DEVICE

BACKGROUND

In today's society, a large percentage of the human and animal population depend on medication for a variety of reasons. Medication may be delivered in a variety of ways, such as, in bottles, blister packs, daily dose packs, nasal mists, inhalers, eye drops, injections and/or in transdermal patches. These different collections of medications may be received from a pharmacy, over the internet or even over the counter. Many medications require a prescription, however, many medications are available over-the-counter without a prescription.

Those who regularly take or administer medication often create systems to remind themselves of when to administer a dose of medication either to themselves, a pet or someone in their care. For many people, memory aids help keep track of dosing such as, for instance; seven day medication reminder boxes that record the time the pill was removed from the box, blister packs that record the time the pill was removed from the package and/or medication reminding systems that perform timer or alarm functions issuing reminders when it is time for a person to take or administer a medication.

DETAILED DESCRIPTION

In the following detailed description, numerous specific details are set forth in order to provide a thorough understanding of claimed subject matter. However, it will be understood by those skilled in the art that claimed subject matter may be practiced without these specific details. In other instances, well-known methods, procedures, and components have not been described in detail so as not to obscure claimed subject matter.

The term 'medication' is used throughout the following disclosure and is intended to refer to any substance used for treatment, control and/or prevention of any human or animal condition, such as, for instance; prevention of disease and/or injury, healing or control of disease and/or injury and/or controlling pain, and claimed subject matter is not limited in this regard. The phrase 'introduced into the body' is used throughout the following disclosure and is intended to refer to delivery of medication into a human or animal body by any of a number of routes, such as for instance; orally, intravenously, intramuscularly, intrathecally, subcutaneously, sublingually, ocularly, nasally, inhalation, cutaneously, and/or transdermally and claimed subject matter is not limited in this regard. The term 'contraindication' is used throughout the following disclosure and is intended to mean one or more factors that render the administration of a medication or the carrying out of a medical procedure inadvisable.

Figure 1:
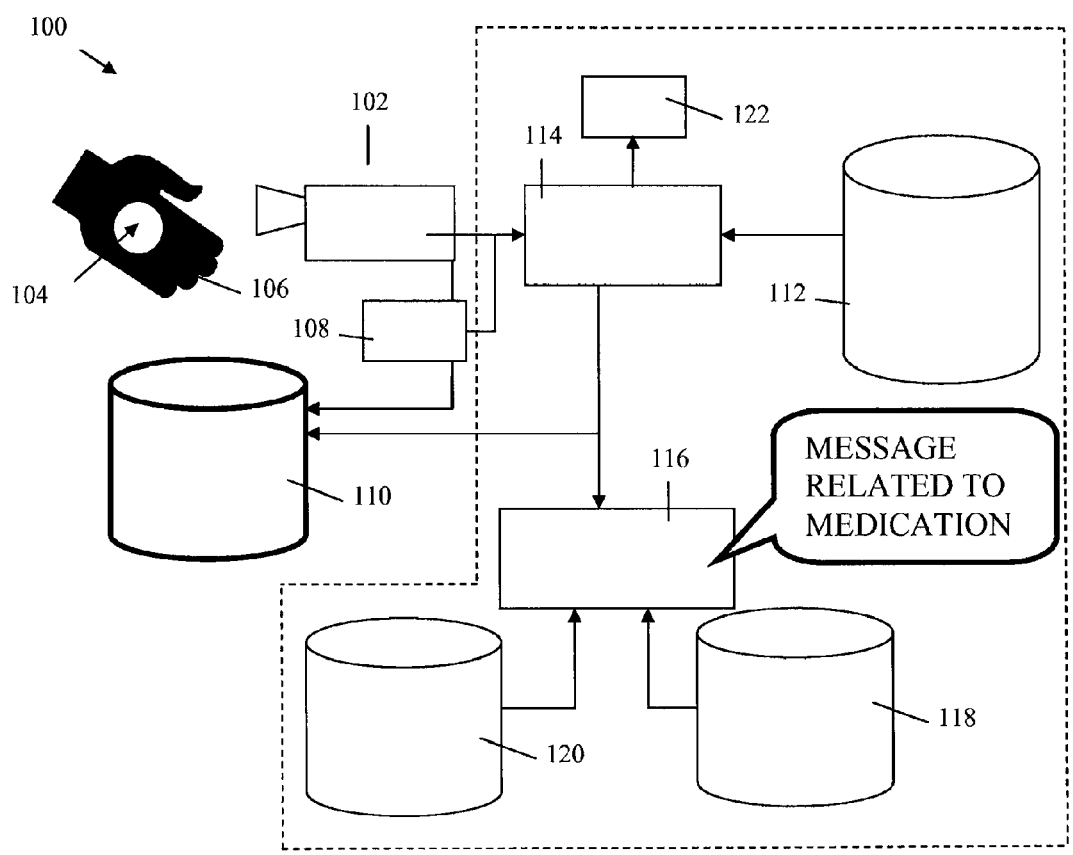
FIG. 1 is a block diagram illustrating a particular embodiment of a medication recording device.

FIG. 1 is a block diagram of a particular embodiment of medication recording device 100. In a particular embodiment, medication recording device 100 may comprise imaging device 102 capable of capturing an image of medication 104 to be introduced into a human or animal body and converting the image to image data for medication identification. Such image data for medication identification may comprise data capable of enabling identification of medication. Identification may be by comparison of converted image data with data in a medication identification database. Such converted image data may comprise any compatible format for comparison with medication identification database data, such as, a cropped version of the image captured, character string, outline coordinates, color coordinates, bar code data, character data and/or a predetermined image file format.

In a particular embodiment, medication 104 may be held in a hand 106 of a user when imaging device 102 is capturing the image or medication 104 may stand alone when imaging device 102 captures the image. In a particular embodiment, when a user is about to take, apply and/or administer a medication, the user may hold medication 104 in their open hand, in front of imaging device 102 and capture an image of medication 104. Activating imaging device 102 to capture an image may be done by a variety of methods, such as; by depressing an activating button, touching a touch screen, activating a motion detector, issuing voice commands, and/or through video processing to detect when a hand is poised for image capture and claimed subject matter is not so limited.

According to a particular embodiment, medication 104 may comprise any of a variety of forms, such as, for instance, pills, liquids, mists, inhalants, drops and/or transdermal patches. In a particular embodiment, a user may capture an image of medication 104 in any form, for instance, in liquid or pill form, liquid in an applicator, an inhaler, package, transdermal patch and/or medication bottle. According to a particular embodiment, various medication forms may have markings, colors, sizes, bar codes and/or other characteristics that may serve as identifiers that may enable human recognition or identification of medication 104 from the image. However, these are merely examples of forms and identifiers a medication may comprise and claimed subject matter is not so limited.

In a particular embodiment, imaging device 102 may comprise any of a variety of devices capable of capturing an image, such as, a traditional camera, a digital camera, an infrared camera, a copier, and/or scanner and claimed subject matter is not limited in this regard. In a particular embodiment, time stamp unit 108 may be coupled to imaging device 102 and may generate a time stamp. According to a particular embodiment, an image of medication 104 may be associated with a time stamp. In a particular embodiment, processor 114 may associate a time stamp with an image or image data generated by imaging device 102. In another embodiment time stamp unit 108 may associate a time stamp with an image of medication 104. According to a particular embodiment, time stamp unit 108 may be coupled to imaging device 102 and processor 114. According to a particular embodiment, an image or image data of medication 104 and the associated time stamp may be stored in non-volatile memory unit 110 which may provide a record of what medications a user has administered, taken, applied or otherwise ingested and when those mediations were administered, taken, applied or otherwise ingested. Such a record may be useful in maintaining a medicinal regimen for humans and/or animals and claimed subject matter is not limited in this regard. In a particular embodiment, such a record may be used by medical personnel or caregivers to enable accurate record keeping of another's medicinal regimen. In a particular embodiment, a record may be reviewed by one's prescriber to either reinforce the instructions to the patient or to adjust the prescription. In the event of an emergency such a record may be valuable diagnostic tool for emergency worker and other medical personnel.

In a particular embodiment, medication recording device 100 may be capable of identifying medication 104. In a particular embodiment, processor 114 may be capable of accessing medication identification database 112. Medication identification database 112 may comprise medication identification parameters. In a particular embodiment, processor 114 may be capable of identifying medication 104 based at least in part on comparing medication identification parameters with the image data of the medication 104 image. According to a particular embodiment, user interface 116 may be coupled to processor 114 and may be capable of communicating a message related to identification of the medication. In a particular embodiment, user interface 116 may comprise a variety of interfaces, such as, for instance; a digital display, an audio output, physical output, tactile output and/or other sensory output and claimed subject matter is not limited in this regard. User interface 116 may display a message describing medication 104, for instance, by digital display, audio output and/or tactile readout (such as brail). In another embodiment, user interface 116 may simply issue a tone, alarm and/or vibration to indicate that medication 104 has or has not been identified.

In a particular embodiment, medication recording device 100 may be capable of verifying that a user is about to take, use, apply and/or administer an approved medication in keeping with a recommended medication regimen. In a particular embodiment, processor 114 may be capable of accessing recommended medication regimen database 118. Recommended medication regimen database 118 may comprise recommended medication regimen parameters. Such parameters may comprise, kind of medication and timing parameters. An increasing number of chronic conditions require the doctor to frequently adjust the patient's dosages, sometimes giving verbal instructions instead of writing a new prescription (e.g., "take your blood pressure pill once every other day now instead of every day"), increasing the chances of a medication-taking error. Medication regimen database 118 may be accessible to medical advising personnel such that when adjustments to a medication regimen are made they may be entered into Medication regimen database 118 thereby reinforcing the new instructions and reducing medication-taking error.

In a particular embodiment, processor 114 may be capable of verifying that the person is about to take, use, apply and/or administer an approved medication in keeping with a recommended medication regimen based at least in part on comparing recommended medication regimen parameters with identified medication 104 and time stamp data of medication 104 image. According to a particular embodiment, user interface 116 may be coupled to processor 114 and may be capable of communicating a message related to verification of conformance to recommended medication regimen. User interface 116 may communicate such a verification message by digital display, audio output and/or tactile readout (such as brail). For example, user interface 116 may say "it's not time yet to take the yellow pills" or "Remember, your doctor told you to only take one of the red pills now." In another embodiment, user interface 116 may simply issue a tone, alarm and/or vibration to indicate that medication 104 is or is not in compliance with a recommended medication regimen.

In a particular embodiment, medication recording device 100 may be capable of determining whether a user is about to take, use, apply and/or administer a contraindicated medication. In a particular embodiment, processor 114 may be capable of accessing medication contraindication database 120. Medication contraindication database 120 may comprise medication contraindication parameters. Such parameters may comprise medication parameters, timing parameters and/or behavioral parameters. In a particular embodiment, a user may be able to input information related to a variety of behavioral variables such as, for instance, whether the individual who is to be administered medication 104 has eaten, exercised, will be driving or has ingested any alcoholic beverage and claimed subject matter is not so limited. According to a particular embodiment, medication recording device 100 may be capable of receiving behavioral variable data from a variety of sources such as physical input by a user, communication from a diagnostic instrument such as blood sugar gages, blood pressure and heart rate monitors and/or breath analyzers and claimed subject matter is not limited in this respect. In a particular embodiment, processor 114 may be capable of determining that the person is about to take, use, apply and/or administer a contraindicated medication based at least in part on comparing medication contraindication parameters with identified medication 104, time stamp data of medication 104 image and/or any behavioral data.

According to a particular embodiment, user interface 116 may be coupled to processor 114 and may be capable of communicating a message related to whether medication 104 is contraindicated. User interface 116 may communicate such a contraindication message by digital display, audio output and/or tactile readout (such as brail). For example, user interface 116 may say, "Because you are taking a cold remedy right now, you shouldn't take the blue pill." In another embodiment, user interface 116 may simply issue a tone, alarm and/or vibration to indicate that medication 104 is or is not contraindicated.

In a particular embodiment, medication recording device 100 may include hand recognition software capable of identifying the individual whose hand appears in the image, in order to infer whether the patient or one of their caregivers are administering medication 104. In a particular embodiment, medication recording device 100 may be implemented in a cell phone comprising a high-resolution camera, speaker, microphone, and network connectivity to provide a mobile medication-taking record. According to a particular embodiment, each time the person is about to take a pill, they hold the pill in front of their cell phone camera and take a picture.

In a particular embodiment, medication recording device 100 may comprise transmitter 122 which may be capable of wirelessly transmitting medication information received from processor 114. In a particular embodiment, processor 114 may be capable of converting medication information into data suitable for wireless transmission. In a particular embodiment, transmitter 122 may communicate medication information to a variety of receiving stations such as, for instance, a router connected to the Internet, a wireless receiver connected to a medic alert system and/or a local or on-site receiver capable of communicating medication information to caregivers such as in an assisted care facility and claimed subject matter is not limited in this regard. According to a particular embodiment, transmitter 122 may communicate a variety of medication related messages such as, simply identifying medication, indicating whether a person is following a medication regimen and/or identify medication contraindications and claimed and claimed subject matter is not limited in this regard.

Figure 2:
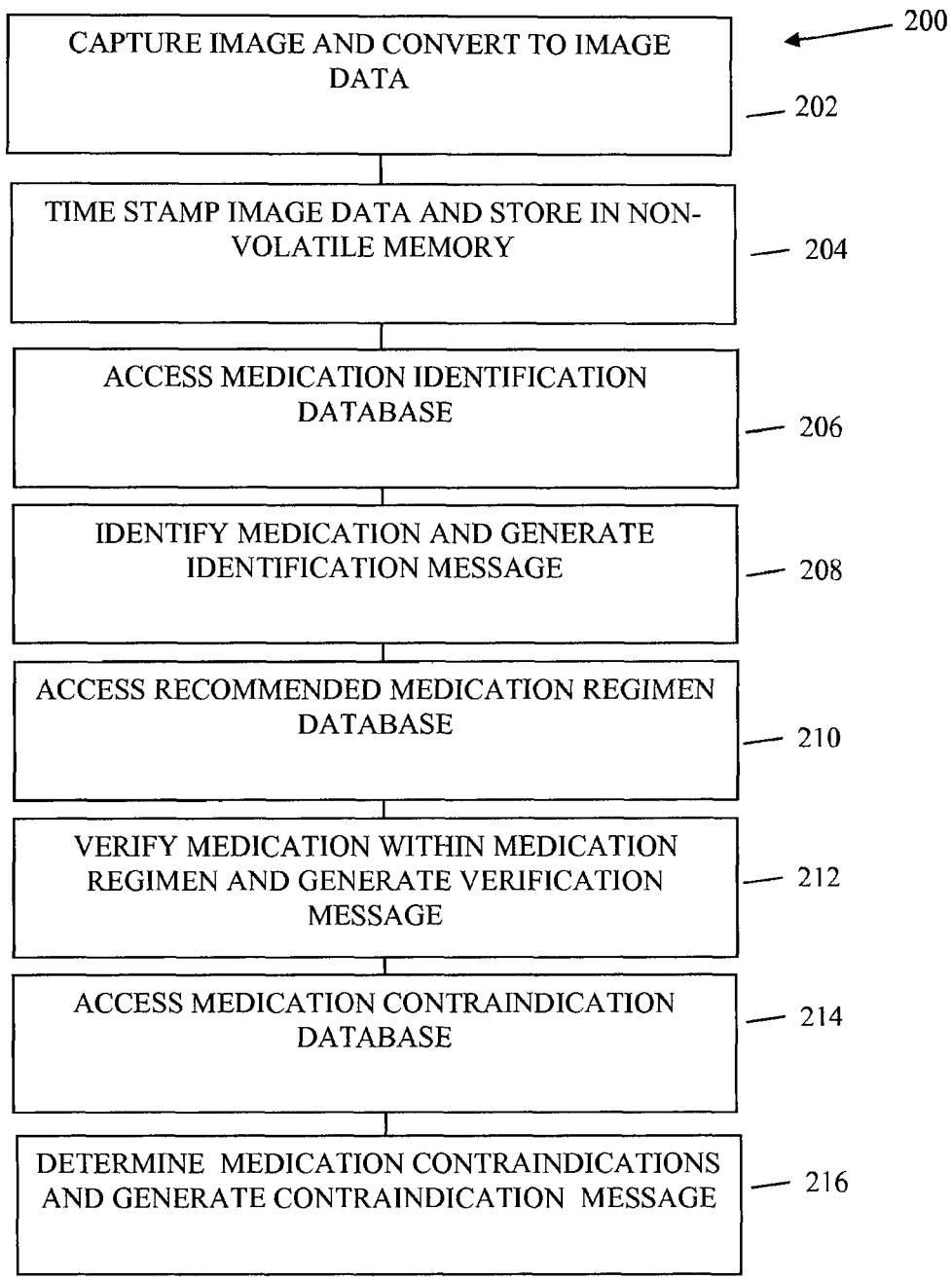
FIG. 2 is a block diagram illustrating a particular embodiment of a medication recording method.

FIG. 2 is a block diagram illustrating a particular embodiment of medication recording process 200. In a particular embodiment, at block 202 an image of a medication to be introduced into a body may be captured and converted to image data. At block 204 the image data may be time stamped and stored. Process 200 may flow to block 206 wherein a medication identification database may be accessed. At block 208, the medication may be identified and a message generated regarding the medication identification. Process 200 may flow to block 210 wherein a recommended medication regimen database may be accessed. At block 212, it may be determined whether the medication to be introduced into the body is in compliance with the recommended medication regimen and a message may be generated regarding compliance with the recommended medication regimen. Process 200 may flow to block 214 wherein a medication contraindication database may be accessed. At block 216, it may be determined whether the medication to be introduced into the body is contraindicated and a message may be generated regarding medication contraindications.

While certain features of claimed subject matter have been illustrated as described herein, many modifications, substitutions, changes and equivalents will now occur to those skilled in the art. It is, therefore, to be understood that the appended claims are intended to cover all such embodiments and changes as fall within the spirit of claimed subject matter.

The invention claimed is:

1. An apparatus, comprising:
   an imaging device configured to:
      generate an image of a medication to be introduced into a body and a hand holding the medication; and
   one or more processors configured to:
      determine identification of a person whose hand appears in the image of the medication and the hand;
      determine identification of the medication based on a comparison of the image of the medication with medication identification data, the medication identification data comprising one or more characteristics related to medications;
      determine whether the identified medication is intended for the identified person; and
      determine, in response to determining that the identified medication is intended for the identified person, whether introducing the identified medication into the body conforms to a recommended medication regime.

2. The apparatus of claim 1, the one or more characteristics related to the medications comprising markings, characters, shapes, colors, sizes, and/or bar codes related to the medications.

3. The apparatus of claim 1, wherein determining whether the identified medication is intended for the identified person comprises determining the identified person is the person to take, use, apply, and/or administer the identified medication.

4. The apparatus of claim 3, wherein the person is a patient, a caregiver, and/or medical personnel.

5. The apparatus of claim 1, further comprising:
   a timestamp unit configured to generate a timestamp indicating a date and time at which the image of the medication and the hand was generated by the imaging device.

6. The apparatus of claim 5, wherein determining whether introducing the identified medication into the body conforms to the recommended medication regime comprises comparing one or more recommended-medication regimen parameters with the identification of the medicine, the identification of the person, and/or the timestamp.

7. The apparatus of claim 1, the one or more processors further configured to communicate, via a user interface, a message related to whether introducing the identified medication into the body conforms to the recommended medication regime.

8. The apparatus of claim 1, further comprising a transmitter configured to communicate a message related to whether introducing the medication into the body conforms to the recommended medication regime.

9. The apparatus of claim 1, further comprising a user interface, wherein the user interface is configured to generate a tactile representation of the identified medication.

10. The apparatus of claim 1, wherein the imaging device is a camera of a mobile device.

11. An apparatus comprising:
    an imaging device configured to:
       generate an image of a medication to be introduced into a body and a hand holding the medication; and
    one or more processors configured to:
       determine identification of a person whose hand appears in the image of the medication and the hand;
       determine identification of the medication based on a comparison of the image of the medication with medication identification data, the medication identification data comprising one or more characteristics related to medications;
       determine whether the identified medication is intended for the identified person; and
       determine, in response to determining that the identified medication is intended for the identified person, whether the identified medication is contraindicated.

12. The apparatus of claim 11, wherein the one or more characteristics related to the medications comprises markings, characters, shapes, colors, sizes, and/or bar codes related to the medications.

13. The apparatus of claim 11, wherein determining whether the identified medication is intended for the identified person comprises determining the identified person is the person to take, use, apply, and/or administer the identified medication.

14. The apparatus of claim 13, wherein the person is a patient, a caregiver, and/or medical personnel.

15. The apparatus of claim 11, further comprising:
    a timestamp unit configured to generate a timestamp indicating a date and time at which the image of the medication and the hand was generated by the imaging device.

16. The apparatus of claim 15, wherein determining whether the identified medication is contraindicated comprises comparing one or more contraindicated medication parameters with the identification of the medicine, the identification of the person, and/or the timestamp.

17. The apparatus of claim 11, the one or more processors further configured to:
    receive a user input indicating whether the identified person has performed and/or will perform an activity; and
    determine whether the identified medication is contraindicated based on the user input.

18. The apparatus of claim 17, wherein determining whether the identified medication is contraindicated based on the user input comprises:
    comparing one or more contraindicated medication parameters with the user input, wherein the one or more contraindicated medication parameters comprise at least a behavioral parameter related to activities including physical activities and/or eating activities; and
    determining whether the activity of the user input matches with one or more of the activities of the behavioral parameter.

19. The apparatus of claim 18, wherein the physical activities comprise an exercise activity, a vehicle operation activity, and/or machinery operation activity.

20. The apparatus of claim 11, further comprising:
a diagnostic instrument configured to generate information related to physical states of the identified person, wherein the diagnostic instrument comprising a blood sugar gauge, a blood pressure monitor, a heart rate monitor, and/or a breath analyzer, and
the one or more processors configured to determine whether the identified medication is contraindicated based on the information related to the physical states of the identified person.

21. The apparatus of claim 11, the one or more processors further configured to communicate, via a user interface, a message related to whether the identified medication is contraindicated.

22. The apparatus of claim 11, further comprising a transmitter configured to communicate a message related to whether the identified medication is contraindicated.

23. The apparatus of claim 11, further comprising a user interface, wherein the user interface is configured to generate a tactile representation of the identified medication.

24. The apparatus of claim 11, wherein the imaging device is a camera of a mobile device.

25. A machine-implemented method comprising:
obtaining, by one or more processors, an image of a medication to be introduced into a body and a hand holding the medication;
determining, by the one or more processors; identification of a person whose hand appears in the image of the medication and the hand;
determining, by the one or more processors, identification of the medication based on a comparison of the image of the medication with medication identification data, the medication identification data comprising one or more characteristics related to medications;
determining, by the one or more processors, whether the identified medication is intended for the identified person; and
determining, by the one or more processors, in response to determining that the identified medication is intended for the identified person, whether introducing the identified medication into the body conforms to a recommended medication regime.

26. A machine-implemented method, comprising:
obtaining, by one or more processors, an image of a medication to be introduced into a body and a hand holding the medication;
determining, by the one or more processors, identification of a person whose hand appears in the image of the medication and the hand;
determining, by the one or more processors, identification of the medication based on a comparison of the image of the medication with medication identification data, the medication identification data comprising one or more characteristics related to medications;
determining, by the one or more processors, whether the identified medication is intended for the identified person; and
determining, by the one or more processors, in response to determining that the identified medication is intended for the identified person, whether the identified medication is contraindicated.

* * * * *